United States Patent [19]

Del Bono et al.

[11] Patent Number: 4,870,166

[45] Date of Patent: Sep. 26, 1989

[54] PROCESS FOR PREPARING HIGH-PURITY DEMATAN SULPHATE, AND PHARMACEUTICAL COMPOSITIONS WHICH CONTAIN IT

[75] Inventors: Rinaldo Del Bono, Milano; Luigi De Ambrosi, Santhià ; Gianni Ferrari; Pier L. Rugarli, both of Milano; Pier G. Pagella, Isola S. Antonio, all of Italy

[73] Assignee: Mediolanum Farmaceutici Srl, Milano, Italy

[21] Appl. No.: 27,733

[22] Filed: Mar. 19, 1987

[30] Foreign Application Priority Data

Mar. 25, 1986 [IT] Italy ................................ 19864 A/86

[51] Int. Cl.$^4$ ..................... A61K 31/72.5; C08B 37/10
[52] U.S. Cl. ......................................... 536/21; 514/56; 536/55.1; 536/55.2; 536/55.3; 536/54
[58] Field of Search ...................... 536/21, 114; 514/56

[56] References Cited

U.S. PATENT DOCUMENTS 3,862,003 1/1975 Okuyama et al. ..................... 536/21
4,783,447 11/1988 Del Bono et al. ..................... 514/56

OTHER PUBLICATIONS

Buddecke et al. *Hoppe-Seyler's Z. Physiol Chem.*, 327:49–64.
Dheu–Andries et al. *Carbohydrate Research* 124:324–322, 1983.

*Primary Examiner*—Joseph L. Schofer
*Assistant Examiner*—Gary L. Kunz
*Attorney, Agent, or Firm*—Stevens, Davis, Miller & Mosher

[57] ABSTRACT

A process for preparing dermatan sulphate (DS) of pharmaceutical purity from animal organs rich in mucopolysaccharides (MPS), by: (a) stabilizing the fresh organs by freezing them either as such or in the form of powder, (b) micronizing the material containing the MPS with an aqueous $CaCl_2$ solution, (c) digesting the homogenate comprising the raw material and the $CaCl_2$ with proteolytic enzymes at alkaline pH and at low temperature, (d) acidifying, heating and filtering the lysate, (e) treating the filtrate with quaternary ammonium salts able to undergo complexing with and thus precipitate either the DS along or all the MPS selectively, (f) recovering and purifying the DA either directly from the ammonium salt complex containing it or from the complex obtained from the mixture of ammonium salt complexes of all the MPS by fractional solubilization with acetone.

17 Claims, No Drawings

PROCESS FOR PREPARING HIGH-PURITY DERMATAN SULPHATE, AND PHARMACEUTICAL COMPOSITIONS WHICH CONTAIN IT

This invention relates to a new process for preparing high-purity dermatan sulphate, and pharmaceutical compositions which contain it as an active ingredient.

Dermatan sulphate (DS) is a mucopolysaccharide (MPS) consisting of repeating disaccharide units of the formula

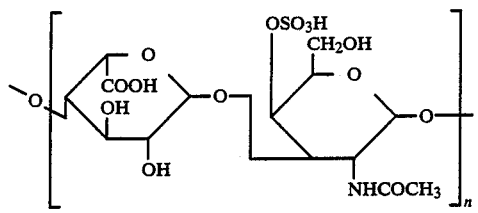

which comprises one mole of iduronic acid and one mole of N-acetyl galactosamine sulphonate, linked by a 1,3 glucoside bond.

The molecular weight of the DS can vary according to the method used for extracting the proteoglycans, and the method used for separating these from the MPS.

The ratio of carboxyls to sulphonic groups, which is theoretically 1:1; can in reality also vary due to the presence of a greater number of sulphonated hydroxyls in some of the galactosamine and iduronic units.

DS has recently aroused considerable interest in that it has been found able to selectively activate heparin cofactor II, and thus to exhibit considerable antithrombin activity, without interfering with the other numerous serine protease inhibitors, which regulate the hemocoagulant processes.

However, the possibility of using it as a drug depends on the possibility of extracting it from natural proteoglycans in a practically unaltered state, without causing degradation or chemical modification of the various groups present, and on practically completely eliminating foreign substances able to give rise to negative side-effects, such as proteins and nucleotides.

From the practical aspect, establishing a DS preparation process satisfying the aforesaid requirements has proved extremely difficult.

Thus study on the extraction of rat skin proteoglycans with inorganic salt solutions at varying concentrations (Chemical Abstracts -vol. 84–1976 - page 194 - abstract 71173d) resulted in the obtention of a mixture of a minor amount of dermatan sulfate with other proteoglycans.

The separation of pure dermatan sulfate from mixtures of glycosaminoglycans is difficult to achieve and it results in a very low yield of the final product.

Also the dermatan sulfate obtained from aqueous solutions of glycosaminoglycans by fractional crystallization at different temperatures (as proposed in the European Patent Application No. 0097625) does not satisfy the requirements for purity.

We have now discovered the subject matter of the present invention, namely a process for extracting DS from animal organs, from which it is obtained practically unaltered in molecular weight and structure from the starting material, and absolutely free from contaminant residues which could cause undesirable side-effects.

The new process comprises the following stages:

(a) selecting the raw material, preferably in the form of bovine or porcine intestinal mucosa, or bovine lung, pancreas, aorta, spleen, brain, thymus or cartilage, and immediately freezing it rapidly in order to prevent alteration;

(b) micronizing the raw material, either as such or homogenized with cold acetone, with an aqueous $CaCl_2$ solution;

(c) enzymatically digesting the aqueous raw material/$CaCl_2$ homogenate with proteolytic enzymes, at alkaline pH and low temperature;

(d) acidifying, heating and filtering the lysate;

(e) treating the clear filtrate with quaternary ammonium salts able to complex the MPS;

(f) selectively filtering off a highly pure DS.

The method of implementing the individual process stages indicated schematically heretofore will now be described in greater detail.

Stage a) involving the preparation of the raw material can be implemented in various ways, all of which are equally appropriate for providing a material suitable for the next stage.

Stage b) involving mixing with $CaCl_2$, which is one of the essential critical stages of the new process, can in fact be implemented in various ways, but these in no way alter the essence of the invention.

In the case of a raw material homogenate frozen as such, it is micronized with an aqueous 0.01 M $CaCl_2$ solution in a raw material:solution weight ratio of 1:0.5.

If the material is to be used in the form of an acetone-treated powder, the initial frozen material is micronized with an aqueous 1 M $CaCl_2$ solution in a material:solution weight ratio of 1:1, the mass is agitated with cold acetone (+5° C.) in a weight ratio of 1:3, filtered and the residue again taken up in cold acetone in a ratio of 1:2, filtered and the residue taken up a further time in cold acetone in a ratio of 1:1. The final residue is dried under vacuum at 35° C., and preserved at low temperature for subsequent enzymatic lysis, or can be passed immediately to the lysis stage by mixing in a suitable reactor with deionized water in a ratio of 1:20.

According to a further alternative, the frozen starting material is micronized with a 0.1 M $CaCl_2$ solution in a raw material: solution weight ratio of 1:10. The mixture is spray-dried with a small-bore rotor and air is introduced at a temperature and exceeding 150° C., with a contact time not exceeding a few seconds. The powder formed in this manner can be preserved in plastic bags at a low temperature for subsequent lysis or can be used immediately by feeding it into a reactor with deionized water in a powder:water weight ratio of 1:20.

If the DS is to be extracted from particularly delicate organs such as the thymus, hypophysis or heart, it can be advantageous to use lyophilisation for small-scale processing. In this case the frozen material is micronized with an aqueous 1 M $CaCl_2$ solution containing 10% of powdered sorbitol, with a raw material:$CaCl_2$ solution weight ratio of 1:1.

After stratification to 2 cm thickness, it is frozen to −40° C. and lyophilised at +25° C., finally using diffusion pumps for residual moisture. The lyophilised product is in the form of a friable powder with a moisture content of about 2%. The lyophilised powder can again be preserved for subsequent lysis, or can be immediately diluted to 1:20 with deionized water to pass to the next stage.

Stage (c) involving enzymatic lysis is characterized by being conducted under particularly mild conditions which prevent any depolymerization or degradation of the DS, using normal proteolytic enzymes such as trypsin, chymotrypsin, and, preferably, alkalase, moxatase and superase.

The aqueous mixture is alkalized preferably with $CaOH_2$, to a pH of between 7 and 9, and is then heated to a temperature of between 40° and 55° C. The enzyme is then added in a raw material:enzyme weight ratio of between 1:0.0001 and 1:0.001. The lysis is continued for between 6 and 24 hours, with continuous electrophoretic checks to determine when the proteoglycan lysis is complete. At this point, the mass is completely fluid.

Said fluid lysate then undergoes stage (d), which comprises slight acidification to a pH of between 3 and 6, preferably by means of HCl (which avoids the introduction of ions other than the chlorine ions already present), but possibly with small quantities of different acids, and heating the fluid mass to 70°-80° C. for about one hour.

The conditions of stage (d) cause protein coagulation and precipitation of the nucleoproteic derivatives in the form of complexes with the Ca salts present. At the same time, the pH and temperature conditions cause the MPS to dissolve in water in the form of Ca salts. The solution is filtered with a rotary filter and possibly further filtered through a filter press to eliminate any traces of salified fatty acids.

In this manner a perfectly clear filtrate is obtained containing only the MPS in the form of Ca salts, and thus practically pure.

This clear solution can either be directly passed to the next stage (e) or, preferably, is first analyzed by electrophoresis to establish the nature and quantity of the MPS present.

As initially stated, stage (e) consists essentially of treating the aqueous solution containing the MPS Ca salts with ammonium salts able to form insoluble complexes with the MPS. However, the object of the present invention is to obtain DS of pharmaceutical purity, and two different alternative procedures are available for this, namely: (1) treating the solution with dimethyl-ethyl-cetyl ammonium ethylsulphate which forms a complex with and selectively precipitates the DS, or (2) treating the solution with a quaternary ammonium salts preferably chosen from the group consisting of Hyamine, cetyl-trimethylammonium bromide and cetyl-dimethylethylammonium bromide, which has the capacity to precipitate all the MPS present in the form of complexes, from which the DS complexes is isolated by selective solubilization with organic solvents.

The choice of one or the other alternative depends essentially on the relative quantity of DS and of other MPS present in the solution, and whether it is intended to recover the other MPS in addition to the DS.

Generally, selective precipitation of the DS in accordance with alternative (1) is preferred.

In order to precipitate with dimethyl-ethyl-cetyl ammonium ethylsulphate, the salt is added to the solution in a weight ratio to the starting raw material of about 1:1500 if this latter is used in the form of a frozen homogenate, or in a weight ratio of 1:300 if it is used in the form of powder. The mixture is allowed to stand for some hours. The DS complex sediments rapidly because of the presence of Ca ions. It is decanted and the complex collected in a centrifuge.

If however it is required to precipitate all the MPS in accordance with alternative 2), the temperature of the clear solution is raised in 60°-70° C., a quantity of ammonium salt equal to the weight of the MPS determined electrophoretically is added, and the mixture diluted with deionized water to lower the solution molarity to 0.4 M.

The mixture is then left standing for 5–12 hours, and centrifuged to recover the precipitated solid complexes. It is then washed with water to remove the excess ammonium salt, and dried.

The selective recovery of high-purity DS in accordance with stage (f) is carried out differently according to whether the precipitation with ammonium salts is accomplished by alternative (1) or (2).

If the DS/dimethyl-ethyl-cetyl ammonium ethylsulphate complex has been selectively precipitated and isolated, said complex is treated with an aqueous 2 M $CaCl_2$ solution containing 10% of ethanol. The weight ratio of DS complex to hydroalcoholic $CaCl_2$ solution is 1:5. The solution is adjusted to pH 7–9 with $CaOH_2$, heated to 60°-80° C. for 1–3 hours, and filtered.

The solution passes to the purification stage, comprising treatment in $20m^2$ spiral columns, with molecular cut-off at 10,000. It is concentrated to 1:10 and to 1:1, these passages being continued until total elimination of the salts and of the last traces of contaminating components. The DS is precipitated from the 10:1 concentrated solution by treatment with acetone in the ratio of 1:0.3 (solution volume:acetone volume) or by treatment with ethanol or methanol in the ratio of 1:0.5. The dermatan sulfate precipitates in the form of a light powder.

The DS obtained in this manner is preferably converted into an alkaline salts by it in a 2 M Na, K, Li or Mg chloride solution, using a DS weight:saline solution volume ratio of 1:10. The mixture of agitated for 2–10 hours, diluted to a ratio of 1:2 with distilled water, filtered and precipitated with acetone in the ratio of 1:0.5.

In this manner, the dermatan sulphate of Na, K, Li or Mg is obtained according to the saline solution used.

If the precipitation with ammonium salts has been carried out in accordance with alternative (2) of stage (e), the DS separation and purification stage f) is carried out in the following manner. The manner of MPS ammonium salt complexes is dispersed at a temperature of about 25° C. for 1–2 hours in acetone.

The DS complex is selectively solubilized in acetone, whereas the other complexes remain undissolved and are separated to undergo separate treatment. The quantity of acetone used is critical in obtaining complete solubilization of the DS complex. If the treated mixture contains 10% of DS complex, 1 volume of acetone (with respect to the volume of the treated complexes) is added. If the mixture contains 20% of DS complex, 2 volumes of acetone are added and so on, thus always using a given ratio of percentage DS content to volume of acetone used.

The mixture treated with the solvent is centrifuged or filtered.

The clear acetone filtrate is treated at ambient temperature with a 3 M saline solution (Na, K, Li or Mg chloride), such that the volumetric ratio of acetone extract to saline solution is between 0.25 and 1.

Under these conditions the DS ammonium complex splits off and is precipitated in the form of the Na, K, Li or Mg salt.

In all cases, the DS salt originating from stage (f) heretofore described has the following characteristics:

single band under electrophoresis in various buffer systems molecular weight: 20,000-40,000
organic sulphur: 6-8%
uronic acids: 30-36%
ratio of sulfate groups to carboxyl groups 1.2-1.5
ratio of uronic acids to galactosamine: 1:1
iduronic acid: 80-90% of the total uronic acids
$[\alpha]D$: $-60°$ to $-65°$
heparin activity: 10 U/mg USP In using the process of the present invention, the DS yield varies according to the original organ or tissue, and is between 1 and 8 kg per 10,000 kg of raw material.

If the other MPS present in the starting material are to be recovered, the procedure used is preferably alternative 2) of stage e), i.e. by total MPS precipitation as ammonium salt complexes.

After solubilizing the DS complex with acetone as described under the preceding point f), the undissolved mass is dispersed in 2 volumes of distilled water to eliminate the acetone residues, is centrifuged and then solubilized-suspended in ethanol following the method described for acetone. Heparin sulphate separates in this manner.

From the mass which remains undissolved in ethanol, and using the same method described for the other solvents, pure heparin is extracted by treatment with methanol.

The sodium, potassium, lithium, calcium or magnesium salts of dermatan sulphate obtained by the process according to the invention are biologically active in activating the so-called heparin cofactor II (about 60 µA IIa/mg) whereas they have no anticoagulant activity on the partial thromboplastin activation time, and have weak factor Xa inhibiting activity (about 20 UAXa/mg).

In vivo, the product is not toxic and does not cause bleeding, but appears to produce considerable vasodilation. It is also active in inhibiting experimental thromboses when administered intravenously, subcutaneously and intraileally, and is able to partly protect animals from damage produced by the administration of Adriamycin.

Topical administration of the product to alterations produced by thrombosis of the superficial venous circle leads to rapid remission of symptoms by virtue of fibrinolytic and anti-inflammatory activity.

The DS obtained by the process according to the invention was evaluated toxicologically and pharmacologically on experimental animals, as described hereinafter.

ACUTE TOXICITY

Acute toxicity was evaluated in the Swiss mouse after oral, intravenous, intra-peritoneal and subcutaneous administration of the dermatan sulphate obtained by the process according to the invention.

The relative $LD_{50}$ values are given in Table 1, and show that dermatan sulphate is of low acute toxicity.

TABLE 1

| Acute toxicity of dermatan sulphate | |
|---|---|
| Method of administration | $LD_{50}$ mg/kg |
| i.v. | 2700 |
| s.c. | 3600 |
| i.p. | >5000 |
| o.a. | >5000 |

TOXICITY BY REPEATED TREATMENT

The toxicity of DS was evaluated after repeated oral and intramuscular administration in the Wistar rat over a period of 5 weeks. The product was administered daily to different groups of rats at doses of 200 mg/kg/day by oral administration and 20 and 40 mg/kg/day by intramuscular administration.

Two groups of rats treated with physiological solution by oral and intramuscular administration respectively were used as controls.

During the treatment period, no behavioral, weight or food consumption changes were observed in the groups of rats treated with DS compared with the groups of rats treated with the vehicle alone.

On termination of treatment the rats were killed under ether anesthesia. The rats treated intramuscularly showed no alteration of the point of injection. There were no significant variations in the hematological, hematochemical or urinary parameters. The rats treated with 40 mg/kg by intramuscular administration showed a slight weight increase of the spleen, but the histological examination showed no damage to the spleen structure.

No further variation was observed in the organs.

ANTITHROMBOTIC ACTIVITY

The antithrombotic activity of DS was evaluated by two experimental thrombosis models. The first, an arteriovenous shunt in the rat in accordance with Umetsu T., Sanai K., Thromb. Haemostas., 39, 1978, 74, gave rise to the formation of a thrombus with mixed venous and arterial characteristics. The second, ligature of the vena cava in the rat in accordance with Reyers et al., Standardization of animal models of thrombosis, 17th Angiological Symposium, Kitzbuhel, Breddin K., Zimmerman Eds. pp 99, 1983, gives rise to the formation of a thrombus with venous characteristics.

1. Arteriovenous shunt

COMPARISON OF DS ANTITHROMBOTIC AND ANTICOAGULANT ACTIVITY

The DS is administered intravenously immediately before activation of the circle in the shunt. On termination of the test the thrombus is removed and weighed. Immediately after measuring the thrombus, blood is collected on the bottom of a test tube and the time required for forming the first coagula on the test tube wall is evaluated (total blood coagulation time).

The results regarding the thrombus weight and coagulation time are shown in Table 2, and demonstrate that dermatan sulphate is able to produce powerful antithrombotic activity. In this respect, even at the minimum dose used (0.125 mg/kg/i.v.) the thrombus weight is significantly reduced. It also has a simultaneous lesser effect on phenomena related to the hemocoagulation processes. In this respect, even to cause modest increases in the coagulation time, which were only statistically but not biologically significant, much greater doses were required than those effective in the antithrombotic sense.

TABLE 2

Comparison of dermatan sulphate antithrombotic and anticoagulation activity "in vivo". Arteriovenous shunt in the rat.

| Dose | Antithrombotic activity | | Anticoagulation activity | |
|---|---|---|---|---|
| mg/kg i.v. | thrombus weight mg | inhibition % | coagulation time sec | increase % |
| 0 | 131.3 ± 11.7 | — | 119.2 ± 4.0 | — |
| 0.12 | 90.5 ± 5.9** | 31 | 112.5 ± 8.5 | — |
| 0.25 | 85.5 ± 3.2** | 35 | 125.7 ± 7.5 | 5 |
| 0.50 | 59.0 ± 5.2* | 55 | 132.5 ± 10.3 | 11 |
| 1.00 | 53.4 ± 4.9** | 59 | 132.1 ± 5.1 | 11 |
| 2.00 | 43.9 ± 2.8** | 67 | 141.3 ± 8.3 ° | 19 |

**p 0.001
* p 0.05

2. Ligature of the vena cava

Comparison of different methods of administration.

The DS was administered intravenously 10 minutes before ligature, subcutaneously 1 hour before ligature, and intraileally 15 minutes before ligature. On termination of the test the thrombus was removed and weighed.

The results are shown in Table 3 and demonstrate that DS is active in inhibiting thrombosis induced by ligature of the lower vena cava in the rat, when administered intravenously, subcutaneously or intraileally. A preliminary evaluation produces dose-effect curves which, at the times considered and for the three methods of administration, namely intravenous, subcutaneous and intraileal, subtend areas which are in the ratio of 1:4:16.

TABLE 3

Antithrombotic activity of dermatan sulphate in the ligature of the vena cava in the rat. Comparison of different methods of administration.

| INTRAVENOUS | | | SUBCUTANEOUS | | | INTRAILEAL | | |
|---|---|---|---|---|---|---|---|---|
| mg/kg | thromb weight mg | inhib % | mg/kg | thromb weight mg | inhib % | mg/kg | thromb weight mg | inhib % |
| 0 | 2.29 ± 0.43 | — | 0 | 4.58 ± 0.50 | — | 0 | 3.20 ± 0.42 | — |
| 0.5 | 1.14 ± 0.31 | 50 | 2.5 | 1.10 ± 0.60 | 76 | 10 | 0.99 ± 0.39 | 69 |
| 1.0 | 0.80 ± 0.32 | 65 | 5.0 | 0.63 ± 0.29 | 86 | 20 | 0.43 ± 0.24 | 87 |
| 2.0 | 0 | 100 | 10.0 | 0 | 100 | 40 | 0 | 100 |

The present invention also relates to pharmaceutical formulations (vials, tablets, capsules, ointments, unguents, syrups, suppositories, drop etc.) containing determined quantities of dermatan sulphate useful in the treatment of surface and profound thromboses. The following formulations are given by way of example:

capsules containing 20-50-100-200 mg of DS;

tablets containing 20-50-100-200 mg of DS plus excipients, deaggregation agents etc. normally used in the pharmaceutical field;

vials containing 20-50-100 mg of DS plus aqueous vehicle;

drops containing 20-50-100-200 mg/ml of DS plus aqueous vehicle, preservatives etc. normally used in the pharmaceutical field;

suppositories containing 20-50-100-200 mg of DS plus excipients normally used in the pharmaceutical field;

ointments containing 20-50-100-200 mg/g of DS plus excipients normally used in the pharmaceutical field.

Some practical embodiments of the process are described hereinafter in order to make the process according to the present invention more easily reproducible.

EXAMPLE 1

10,000 kg of frozen bovine and porcine intestinal mucosa were micronised and transferred into a reactor containing 5,000 l of an aqueous 0.01 M $CaCl_2$ solution.

The mass was kept agitated at 70 rpm until completely homogenised, after which the pH was adjusted to 7 with a $Ca(OH)_2$ solution and heated to 45° C.

10 kg of alkalase homogenate in 50 l of water were added, and the mixture kept at a temperature of 45° C. for 12 hours under continuous agitation. At the end of this period, hydrochloric acid was added to the fluid mass until pH 4 was reached, after which it was heated to 90° C. for 30 minutes.

The solution was filtered through a filter press prepared with celite, and the clear solution was transferred into a reactor and filtered through a press with clarifying cards. About 12,000 liters of totally clear solution were obtained, and to this 10 l of dimethyl-ethyl-cetyl ammonium ethylsulphate dissolved in 100 liters of water were added in small doses under agitation.

After sitting for 6 hours, the clear solution was decantered and the residue recovered in a Toniatti centrifuge at 10,000 rpm.

The collected complex was poured into 1000 l of a 2 M $CaCl_2$ solution containing 100 l of ethanol. It was adjusted to a pH of about 8 by adding a saturated $Ca(OH)_2$ solution and heated to 80° C. for about 2 hours under slow agitation. After adding 10 kg of a filter aid, the mixture was filtered through a press until the solution was clear. The liquid (1200 l after washing the cake) was fed to ultrafiltration through spiral columns (20 m$^2$) with cut-off at 10,000. After concentrating to 200 liters, it was diluted to 1000 liters and again concentrated to about 100 liters. This operation was continued until the permeate was practically negative towards Ca salts.

30 liters of acetone were added to the solution to precipitate the DS. The precipitate was collected, washed in acetone and dried.

Yield: 8 kg in the form of anhydrous powder.

The powder was agitated in 80 l of 2 M NaCl solution (125) for 1 hour, after which the solution was diluted to 150 liters, filtered and precipitated with 45 liters of anhydrous acetone.

The precipitate was collected on a filter press, washed with a 40% aqueous acetone solution and dried under vacuum.

Yield: 7 kg of DS sodium salt.

The powder was dissolved in 100 l of deionized water, decolored by passing over an anionic resin, depyrogenated under hot conditions overnight, precipitated with 1:1 acetone, filtered and lyophilized.

Yield: 4 kg of DS having the following characteristics:

M.W. 35,000
$[\alpha]_D - 65°$
ratio of sulphate groups to carboxyl groups 1.25
ratio of uronic acids to galactosamine 1:1
single band under electrophoresis

EXAMPLE 2

1000 kg of acetone powder obtained from bovine pancreas and lung are micronized with an aqueous 0.01 M $CaCl_2$ solution and diluted with a 0.01 M $CaCl_2$ solution to a volume of 20,000 liters.

After mixing for about 30 minutes and heating at 45° C., 10 kg of moxatase homogeneate in 50 l of water were added, and the temperature maintained at 45° C. for 12 hours under continuous agitation.

The procedure described in Example 1 was followed exactly.

Yield 5 kg of DS having the following characteristics:
M.W. 40,000;
$[\alpha]_D - 65°$
ratio of sulphate groups to carboxyl groups 1.2;
ratio of uronic acids to galactosamine 1:1;
single band under electrophoresis.

The procedure and results are identical if starting from powder of the said organs obtained by spray-drying.

EXAMPLE 3

100 kg of a mixture of frozen fresh animal organs (lungs, vessels and intestine) were ground to obtain a pulp which was fed into a reactor containing 50 l of an aqueous 0.01 M $CaCl_2$ solution.

The mass was kept under agitation until completely homogenized, was then adjusted to pH 7.2 with Ca-$(OH)_2$, and heated to 50° C.

200 l of an enzymatic solution containing 0.05% by weight of superase and heated to 50° C. were then added.

The mixture was kept under agitation at 50° C. for 8 hours. After this time the lysis was terminated. The mixture was acidified to pH 5 with HCl, heated to 80° C. and filtered under hot conditions using a filter earth as filter aid.

A filtrate sample was analyzed to determine the MPS content, and in particular the DS content in order to calculate the quantity of quaternary ammonium base and organic solvent to be used in the subsequent stages. The analytical determination was carried out by the following procedure:

10 ml of filtrate were concentrated to 1 ml and distilled water was then added to a total volume of 2 ml. A plate of 3% agarose for electrophoresis in a buffer solution consisting of barium acetate and acetic acid was prepared separately. 5-10 μl of the sample under examination were deposited on this plate and a first electrophoresis was carried out at 15 volts/cm (about 120 volts). A second electrophoresis was then carried out in a buffer solution of propanediamine under the same conditions and the plate was dried by an infrared source. It was dyed with 2% toluidine blue, and decolored with 5% acetic acid.

At this point a photodensitometric reading was taken, and the individual MPS areas were measured, by comparison with a reference standard.

The analytical determination of the MPS showed a total of 200 g with a dermatan sulphate content of 50 g.

On the basis of the analytical data, 200 g of Hyamine were added to the filtrate.

The filtrate was agitated at 70° C. for 1 hour and diluted with deionized water, to adjust the solution molarity to 0.4 M.

It was left standing for 5 hours, and the precipitate in the form of a mixture of MPS complexes with the quaternary ammonium salt was recovered by centrifuging.

This precipitate, of buttery appearance, was first washed with water to eliminate the excess salt, after which 1 liter of acetone was added while keeping the suspension under agitation for 3 hours at ambient temperature, to obtain selective solubilization of the dermatan sulphate complex. The suspension was centrifuged to obtain about 1 liter of DS solution 2 liters of a 3 M NaCl solution were added to the DS solution, followed by 2 liters of acetone, to precipitate the DS. The DS was separated by centrifuging, washed with ethanol and dried.

In this manner 50 g of dry DS were obtained having the following characteristics:
M.W. 35,000;
$[\alpha]_D - 60°$
ratio of sulphate groups to carboxyl groups 1.5;
ratio of uronic acids to galactosamine 1:1;
single band under electrophoresis

EXAMPLE 4

The residual solid material resulting from the selective solubilization of the DS complex obtained by treating the MPS mixture as described in Example 3 was dispersed in 500 ml of distilled water in order to eliminate the acetone residues, which were removed together with the water by centrifuging.

The insoluble precipitate was treated with 1.8 liters of ethanol, maintaining the obtained suspension under agitation for 3 hours at a temperature of 50° C. to obtain selective solubilization of the herparin sulphate complex.

The subsequent procedure for obtaining the herparin sulphate was carried out as described for the dermatan sulphate of Example 3.

60 g of herparin sulphate were obtained having the following characteristics:
M.W. 30,000;
$[\alpha]_D + 55°$;
single band under electrophoresis.

EXAMPLE 5

The residual solid material resulting from the selective solubilization of the herparin sulphate complex obtained by the treatment described in Example 4 was dispersed in 3 l of distilled water to eliminate the ethanol residues, and was then centrifuged.

The insoluble precipitate was treated with 5 l of methanol, maintaining the obtained suspension under agitation for 3 hours at a temperature of 50° C. to obtain solubilize of the heparin complex.

The subsequent procedure for obtaining and purifying the heparin was carried out as described for the DS of Example 3.

In this manner 50 g of pure heparin were obtained, of pharmaceutical specification.

We claim:

1. A process for preparing dermatan sulphate (DS) of pharmaceutical purity from fresh animal organs rich in mucopolysaccharides (MPS), comprising:
    (a) stabilizing the fresh organs by freezing them either as such or in the form of powder,
    (b) micronizing the stable material containing MPS with an aqueous $CaCl_2$ solution to form a homgeneate, (c) digesting the homogenate comprising the stable material and the $CaCl_2$ with proteolytic enzymes at alkaline pH and at low temperature to form a lysate, (d) acidifying, heating and filtering the lysate, (e) treating the filtrate with quaternary ammonium salts to complex with and thus precipitate either the DS alone or all the MPS selectively, and (f) recovering and purifying the DS from the ammonium complex.

2. A process as claimed in claim 1, wherein the micronizing is carried out on frozen stable material mixed with an aqueous 0.01 M $CaCl_2$ solution in a weight ratio of 1:1.

3. A process as claimed in claim 1, wherein the micronization is carried out on frozen stable material mixed with an aqueous 1 M $CaCl_2$ solution in a weight ratio of 1:1, and the micronized organs are repeatedly treated with cold acetone and filtered, and finally dried.

4. A process as claimed in claim 1, wherein the micronization is carried out on frozen stable material mixed with an aqueous 0.1 M $CaCl_2$ solution in a weight ratio of 1:1, and the mixture obtained is spray-dried with air at a temperature of less than 150° C.

5. A process as claimed in claim 1, wherein the micronization is carried out on frozen stable material mixed with an aqueous 1 M $CaCl_2$ solution containing 10% of sorbitol, in a weight ratio of 1:1, and the mixture obtained is lyophilized.

6. A process as claimed in claim 1, wherein the digesting with proteolytic enzyme comprising adding the enzyme to the micronized mixture diluted with water, adjusting to pH 7-9 and heating to 40°-55° C.

7. A process as claimed in claim 6, wherein the enzyme is added in a weight ratio of stable material to enzyme of between 1:0.0001 and 1:0.001.

8. A process as claimed in claim 6, wherein the pH is adjusted to between 7 and 9 with $Ca(OH)_2$.

9. A process as claimed in claim 1, wherein the lysate is acidified to a pH of between 3 and 6 and heated to 70°-90° C.

10. A process as claimed in claim 9, wherein the lysate is acidified with HCl.

11. A process as claimed in claim 1, wherein the filtered lysate is treated with dimethyl-ethyl-cetyl ammonium ethylsulphate to selectively precipitate a DS complex.

12. A process as claimed in claim 1, wherein the filtered lysate is treated with a quaternary ammonium salt selected from the group consisting of Hyamine, cetyl-trimethyl ammonium bromide and cetyl-dimethyl-ethyl ammonium bromide, at a temperature of 60°-70° C., to precipitate in the form of complexes all the MPS present.

13. A process as claimed in claim 12, wherein the DS complex is selectively solubilized with acetone.

14. A process as claim in claim 11, wherein the DS is recovered from the ammonium complex by treating the ammonium complex with an aqueous 2 M $CaCl_2$ solution containing 10% ethanol, adjusting the pH to between 7 and 9 and heating to 60°-80° C.

15. A process as claimed in claim 13, wherein the DS is recovered from the ammonium complex by treating with a 3 M saline solution, using a volumetric ratio of acetone extract to saline solution of between 0.25 and 1.

16. A process as claimed in claim 13, wherein the residue from the acetone treatment is treated with ethanol to selectively solubilize a heparin sulphate complex.

17. A process as claimed in claim 16, wherein the residue from the treatment with ethanol is treated with methanol to selectively solubilize the heparin complex.

* * * * *